US010682097B2

(12) United States Patent
Bruno et al.

(10) Patent No.: US 10,682,097 B2
(45) Date of Patent: Jun. 16, 2020

(54) PEOPLE MONITORING AND PERSONAL ASSISTANCE SYSTEM, IN PARTICULAR FOR ELDERLY AND PEOPLE WITH SPECIAL AND COGNITIVE NEEDS

(71) Applicants: Dotvocal s.r.l., Genoa (IT); Universitá degli Studi di Genova, Genoa (IT); Teseo S.r.l., Genoa (IT)

(72) Inventors: Barbara Bruno, Genoa (IT); Antonella Giuni, Genoa (IT); Fulvio Mastrogiovanni, Genoa (IT); Enrico Reboscio, Genoa (IT); Antonello Scalmato, Genoa (IT); Antonio Sgorbissa, Genoa (IT)

(73) Assignees: UNIVERSITÁ DEGLI STUDI DI GENOVA, Genoa (IT); TESEO S.R.L., Genoa (IT)

( * ) Notice: Subject to any disclaimer, the term of this patent is extended or adjusted under 35 U.S.C. 154(b) by 0 days.

(21) Appl. No.: 16/072,870

(22) PCT Filed: Feb. 3, 2017

(86) PCT No.: PCT/IB2017/050604
§ 371 (c)(1),
(2) Date: Jul. 25, 2018

(87) PCT Pub. No.: WO2017/134622
PCT Pub. Date: Aug. 10, 2017

(65) Prior Publication Data
US 2018/0368780 A1    Dec. 27, 2018

(30) Foreign Application Priority Data
Feb. 4, 2016  (IT) .................. 102016000011204

(51) Int. Cl.
*A61B 5/00*   (2006.01)
*A61B 5/11*   (2006.01)
*G08B 21/04*  (2006.01)

(52) U.S. Cl.
CPC .......... *A61B 5/7264* (2013.01); *A61B 5/1113* (2013.01); *A61B 5/1116* (2013.01);
(Continued)

(58) Field of Classification Search
None
See application file for complete search history.

(56) References Cited

U.S. PATENT DOCUMENTS 7,962,981 B2 * 6/2011 Lemire .................. A61G 7/005
                                                          5/616
9,861,543 B2 * 1/2018 Madsen ................. A61G 7/018
(Continued)

OTHER PUBLICATIONS

Pirzada et al., Sensors in Smart Homes for Independent Living of the Elderly, 2018, IEEE, 978-1-5386-6594 (Year: 2018).*
(Continued)

*Primary Examiner* — Carlos Garcia
(74) *Attorney, Agent, or Firm* — Themis Law (57) ABSTRACT

A system for monitoring and private assistance to people includes sensors that detect descriptive parameters of environmental conditions, and sensors and/or devices that monitor a person's position and, optionally, her physiological parameters. In particular, the system includes sensors and/or devices that monitor a person's position at the topological level and generate tracking signals in time and within a digital topological model of the environment; sensors that monitor posture and/or its variations in time and that provide status signals corresponding to predetermined postures and/ or signals, indicating posture variations in time, which are processed by a logic control unit and software that evaluates position and posture and its variation in time and that
(Continued)

classifies the signals according to predetermined categories of motor and/or postural activities, and that performs a comparison between detected parameters and predefined patterns of execution.

11 Claims, 3 Drawing Sheets

(52) U.S. Cl.
 CPC ............ *A61B 5/4088* (2013.01); *A61B 5/746* (2013.01); *G08B 21/043* (2013.01); *G08B 21/0423* (2013.01); *A61B 2503/08* (2013.01)

(56) References Cited

U.S. PATENT DOCUMENTS

| | | | |
|---|---|---|---|
| 2003/0058111 A1 | 3/2003 | Lee | |
| 2007/0208263 A1* | 9/2007 | John | ............... A61B 5/0452 600/509 |
| 2010/0145234 A1 | 6/2010 | Jang | |
| 2012/0265104 A1 | 12/2012 | Menegon | |
| 2016/0267759 A1* | 9/2016 | Kerzner | ........... G08B 13/19645 |
| 2017/0187737 A1* | 6/2017 | Zhang | ................. H04L 63/1425 |
| 2019/0057561 A1* | 2/2019 | Zavesky | ............ G07C 9/00079 |

OTHER PUBLICATIONS

Shin et al., Detection of Abnormal Living Patterns for Elderly Living Alone Using Support Vector Data Description, 3, May 2011, IEEE, IEEE Transactions on Information Technology in Biomedicine, vol. 15, No. 3, pp. 438-448 (Year: 2011).*

* cited by examiner

PEOPLE MONITORING AND PERSONAL ASSISTANCE SYSTEM, IN PARTICULAR FOR ELDERLY AND PEOPLE WITH SPECIAL AND COGNITIVE NEEDS

FIELD OF THE INVENTION

This invention is related to a people monitoring and personal assistance system, in particular elderly and people with special or cognitive needs, which system includes a number of sensors to determine descriptive parameters of the environment where the person is, and a number of sensors to determine at least the person's position in such environment and possibly the person's physiological parameters, as well as movements of the person.

BACKGROUND OF THE INVENTION

Currently, systems to monitor people in specific environments, mostly limited by structural boundaries, for instance apartments, or closed environments, walled gardens or similar, assume to determine a person's position within the aforementioned environment with respect to an environment's topographic map and possibly to determine the person's physiological parameters using sensors, which are indicative of the person's well being.

Such systems, although apt for the goals they address, are nonetheless inappropriate for a real and proper monitoring function for a person's conditions to the aim of assistive purposes, above all for what concerns determining both physical, neurological and cognitive health conditions, and are incapable at all of rapidly and early determining emergency conditions such as possible cognitive pathologies or a decline in the monitored people's motor capabilities, since they do not correlate, in an algorithmic and systematic way, information coming from sensors neither with time nor with rules able to describe quantitatively states of well being and states of danger.

SUMMARY OF THE INVENTION

The goal of the present invention is to realize a new welfare paradigm with a system able to monitor people's activities, both with respect to their positions in the environment, and with their postures, and with respect to the temporal evolution of said postures, and with respect to temporal relations between the said activities, for each single person even if more than one is present in the environment.

An additional goal is to refine the system to allow for the monitoring of a possibly elderly person living alone in an apartment or in assisted-living facilities, who can suffer from mild cognitive, neurological or physical disabilities.

An additional goal is to achieve an easy-to-use and cheap system.

Yet an additional goal is to achieve the aforementioned system adopting a modular architecture, whose components may be constituted by commercially available, components off-the-shelf hardware.

Additional goals are related to the achievement of a system characterized by:

ease of installation and configuration in pre-existent environments, with a limited human intervention;

ability to automatically raise alarms to medical personnel or to non-cohabitant relatives, neighbors, firemen, depending on the alarm's gravity and type;

ability to dialogue (using voice and/or gestures and/or simple actions) with the person in order to obtain proactively information about his/her state, and his/her actions adaptability to a person's status, considering also the progressive degradation of their cognitive, neurological and physical disabilities;

intrinsic safety characteristics, as to say, an alarm is always activated unless the system has proven the absence of danger;

identification of inappropriate behaviors, with the aim of tracking the evolution of cognitive and/or physical disorders, as well as identifying potentially dangerous situations.

The present invention achieves the aforementioned goals with a system of the kind described at the beginning, in which are envisioned:

sensors and/or devices to determine the assisted person's position at a topological level, which generate the assisted person's position tracking signals over time and within a digital topological model of the environment where the said person is located and in particular lives;

sensors to determine the assisted person's posture and/or its variation over time, which provide state signals corresponding to previously established assisted person's postures and/or their variation over time;

possibly, but not necessarily, sensors to monitor physiological parameters of the assisted person, and/or the variation of such parameters over time;

an elaboration unit configured to execute an algorithm with instructions executable by the said elaboration unit, providing the following steps:

it acquires signals from aforementioned sensors over time, translates them into information described in a form of symbolic logic;

it memorizes such symbols in a taxonomic data structure divided into two parts, terminological and assertional;

it classifies said data basing on terminological models, defined in a form of symbolic logic;

it uses a series of dialogues with the assisted person in case the aforementioned classifications fail in the sense they do not correspond to none of the memorized terminological models, in order to acquire further information to improve classification;

it verifies if such classifications correspond to any state of the assisted person described as potentially dangerous, or even uncommon or unforeseen;

it generates suitable alarms in case of dangerous states or uncommon or unforeseen situations, otherwise it continues acquiring data from sensors and/or the dialogues.

According to an executive form, the signals of said sensors are represented by logical symbols with boolean values (true/false), and possibly with multiple truth values (e.g., fuzzy) and/or probabilistic.

Yet another executive form uses a data structure which is based on the formalism called Descriptive Logics or a formalism of equivalent expressive power.

In another executive form, symbols can be grouped and put into relation each other, and the related temporal information can be put into relation with them.

Classification can be performed using standard reasoning mechanisms, typical of Descriptive Logics, as well as by reasoning mechanisms with similar inferential power, like the so-called "instance checking" and the so-called "subsumption", as well as by the methods with equivalent capabilities in other aforementioned representation systems.

In an executive form the dialogue can be formalized using formal grammars methods, and dialogue models represented in the taxonomic data structure, and even using speech comprehension and generation systems commercially available; the outcomes of the dialogue process are themselves represented by logical symbols over time, as boolean values (true/false), possibly with multiple truth values (e.g., fuzzy) and/or probabilistic, being such outcomes used by the classification process.

According to a further characteristic, determining dangerous states of the assisted person, as well as uncommon events, can be achieved by comparing symbols in the assertional structure with predefined symbols defined in the terminological structure.

An executive form implements alarms using suitable commercial systems.

An executive form uses an algorithm that performs an evaluation of symbols representing signals related to position and posture of the assisted person and their relevant variations over time, as well as symbols representing physiological parameters and their relevant variations over time; the mentioned algorithm classifies such symbols following predefined schemes stored in the terminological part of the data structure; the aforementioned symbols can be put into relation formally with motor and/or postural activities and/or physiological parameters behaviors, represented in the terminological structure, as well as models and/or descriptions of actions of the assisted person, composed either sequentially and concurrently, by simpler actions over time.

A further executive form includes an algorithm able to compare the schemes stored in the terminological part of the data structure with the symbols corresponding to data acquired by sensors by using also parameters chosen at least among the following: position of the monitored person and/or his/her posture and/or his/her physiological parameters and/or the velocity of variation of the aforementioned three ones, and/or the temporal duration of such variations and/or the absence of such variations and/or the congruity of postures with actual positions in the environment with respect to the same parameters related to the models stored in the terminological part of the data structure which describe the actual motion activities or postural states.

An executive form includes an algorithm able to compare schemes stored in the terminological part of the data structure, associated to physiological parameters, with the symbols to data acquired by sensors by using also parameters chosen at least among the following: body temperature of the monitored person and/or his/her blood pressure and/or his/her heart rate and/or the velocity of variation of the aforementioned three ones, and/or the temporal duration of such variations and/or the absence of such variations a with respect to the same parameters related to the models stored in the terminological part of the data structure.

The predefined behavioral model, stored in the terminological part of the data structure, can be personalized using a training phase in which information about the peculiar behavioral features of the monitored person are collected, which correspond to common behavioral conditions.

Such training or personalization can take place at the installation or set up phase, by a simple textual and/or graphical interface, or/and by implementing the classification program as an algorithm, for instance a neural network or any other algorithm with comparable expressive and computational capabilities, able to execute learning steps during its execution since the set up phase.

According to another improvement, the system envisions that data related to position and movement of the monitored person in the environment and/or of posture and its variation can be integrated with data related to the monitored person's physiological parameters, acquired by sensors, possibly commercially available, such as temperature, blood pressure, heart rate and/or cardiac traces and other physiological parameters.

Another executive form of the system can foresee that data related to environmental conditions, such as temperature, humidity, luminosity level, atmospheric pressure, presence of smoke and/or or dangerous and/or harmful gases and similar, occurrence of noises and source type or effect of noise production, be combined as well.

Thanks to symbols corresponding to these additional data, the algorithm can be defined as a control procedure that refines the classification of the detected activities on the basis of data related to the position in the environment and/or its variation and/or to data related to the posture and/or its variation with the monitored person's physiological parameter data and/or also data related to environmental conditions, therefore improving the accuracy of the analysis and the classification of symbols describing the state of the monitored person.

When the classification of symbols and/or of combinations of symbols and/or of temporal sequences of symbols indicates a condition of anomalous behavior of the monitored person, or a behavior outside the usual behavioral schemes and/or a dangerous situation, it is possible to automatically generate alarms to send to a series of persons and/or organizations selected during the configuration or installation phase (e.g. relatives, medical or trained or emergency personnel, firemen, neighbors, and so on) who is specifically trained to intervene to deal with the conditions detected by the classification procedure itself.

It is also possible to foresee in the system either passive communication means to interact with the monitored person, for example with the emission of messages using devices distributed in the environment, such as a series of monitor, a radio, a TV set, or a speaker system, or similar digital devices.

If the classification procedure detects an anomalous behavioral condition of the monitored person, or outside the common behavioral schemes, and/or a dangerous situation, possibly related to physiological conditions then the system allows for intervening in an automated and quick way, with the best possible use of available interaction technologies and devices.

Furthermore, by periodically classifying symbols and/or combinations of symbols and/or the related temporal sequences corresponding to the assisted person's activities, it is also possible to measure the evolution of the same person's cognitive capabilities and/or physiological conditions, therefore being able to pro-actively intervene not only to safeguard the said person from a sudden dangerous condition in a short time period, but also to set the necessary therapeutic ground to deal with worsening conditions, when the pathology is still in its onset.

In the present invention the term "dialogue" is defined as an interaction between the system and the assisted person, possibly repeated several times, in which the system sends vocal messages to the said person waiting for a response by the person.

Several kinds of responses are possible, that can be executed in alternative or in combination, consisting either in a vocal response or in the execution of a movement detected by a sensor (like a gesture or moving to a different place).

In an executive form, the interpretation of the response can give an information represented by the system as a symbol, which, like other symbols, is put into relations to other symbols, including temporal representations, and suitably classified.

Following a further characteristic, the datum coming from a dialogue reply can be used to generate a symbol that describes a variation with respect to other symbols; such symbol can, after its classification, make the algorithm generate further and iterative messages waiting for a response by the monitored person.

The dialogue iterative phase consists of the abovementioned steps; in more details, they consist of a sequence of messages sent by the system and series of responses by the monitored person until:

the system is able to decide that the situation does not require further response, or the monitored person's state is classified as safe, or the system decides that an alarm is necessary.

Following a further characteristic, an alarm is generated in any case the number of iteration in the dialogue phase has exceeded a given safety value without concluding that the monitored person's state is safe, so that the algorithm has characteristics of intrinsic safety with respect to the monitored person.

An example of the system's execution according to the present invention foresees a four-layer modular and scalable architecture, such as:

i. a level is constituted by the hardware infrastructure;

ii. a level is constituted by the algorithm coded in the software executed as series of operative instructions by the aforementioned hardware infrastructure implementing the classification procedure based on the taxonomic structure and the dialogue;

iii. a level with a database of symbols representing models and/or schemes of behaviors, of symbols describing some environment characteristics, of symbols referring to possible dialogues described in a logical formalism based on Description Logics, the present level including:

a. models combining sensor data with suitable symbols and/or combinations of symbols and/or temporal sequences of symbols related to actions executable by the assisted person and his/her postures, like for example "standing", "sitting", "walking", "lying", performing common everyday tasks and so on;

b. models combining sensor data with suitable symbols and/or combinations of symbols and/or temporal sequences of symbols related to typical habits of the monitored person, in particular every day routine activities like "sleeping", "cooking", "eating", "using the bathroom", "watching television", "reading", "going outside" and so on, together with related temporal information and schedules in time;

c. a model representing an environment in which the assisted person lives and acts, in which the most relevant characteristics are represented as symbols and/or combinations of symbols and/or temporal sequences of symbols, specifically suited to localize the monitored person at topological level; the kind of environments taken into account are those considered in this invention, e.g. every day living environments;

d. models which encode normative aspects related to healthy behaviours of an assisted person, using symbols and/or temporal sequences of symbols; such normative definitions can be used to determine if symbols and/or temporal sequences of symbols representing data coming from sensors in the assertional part of the data structure correspond to potentially dangerous situations and/or to the assisted person's bad habits;

e. rule-based models that, on the basis of the classification of symbols and/or of the combinations of symbols and/or of the temporal sequences of symbols in the assertional part of the data structure can generate alarms and/or messages and/or receive answers for dialogues with the assisted person;

f. models, possibly rule-based, and possibly based on structures typical of formal grammars for encoding dialogues with the assisted person by means of suitable symbols and/or suitable combinations of symbols and/or suitable temporal sequences of symbols in the terminological part of the data structure;

iv. a communication/data sharing level among the system's hardware devices and with external systems with respect to the considered system, such as external communication networks, computers, smartphones and other digital devices.

The hardware is advantageously constituted by a series of modular devices, at least one part of which is wearable, to distribute in the environment. The hardware devices communicate with each other using different possibly wireless modalities and can in part be developed ad hoc, and partially are constructed in a personalized way, while partially can be interfaced with commercially available devices or use such devices.

The choice of the type and number of the hardware devices adheres to the principle of cost minimization, identifying the minimum set of such devices able to meet the goal performance with respect to the contingent situation related to the system use, complying the before mentioned principle of intrinsic safety, but allowing at the same time for expansions and adjustments as well as an effective energetic autonomy; the adopted technologies are the most up-to-date provided they are reliable and with a meaningful utilization horizon.

According to the present invention, the system therefore implements an algorithm which, using also procedures for classification on data structures based on Description Logics or logical formalisms of comparable or higher expressive capacity, in order to classify symbols and/or temporal sequences of symbols in the assertional part of the data structure, is able to determine if such symbols and/or combinations of symbols and/or temporal sequences of symbols correspond to models described in the terminological part of the data structure, and decides whether to activate a dialogue procedure with the assisted person to acquire further symbols and/or combinations of symbols and/or temporal sequences of symbols, so definitely being able to activate or not alarm procedures, for example to alert medical personnel or not cohabiting relatives, neighbours, firemen etc. according to the alarm's type and severity. In particular the algorithm can analyze symbols and/or combinations of symbols and/or temporal sequences of symbols corresponding to the acquired data from sensors and represented in the assertional part of the data structure, hence classifying them as either compatible or not compatible with normed behaviours in every day life, and/or with habits specific to the assisted person.

Therefore, the system defined in the present invention is able to understand the assisted person's wellness level on the basis of his/her habits and personalized parameters, to foresee anomalous and potentially dangerous situations, to promptly intervene in case of danger, to dialogue with the person to increase its understanding of what is happening, to store meaningful data for a further successive assistance, to understand gestures, motion, same person's position, to learn calibrated modifications of common habits, to manage help requests to the outside, to assure a personalized adaptation also by not trained personnel, such as the monitored person's relatives or other.

With respect to the taxonomic data structure, formalisms like Description Logic can be used, or equivalent ones from the point of view of the formal expressivity and of the computational capabilities.

The taxonomic database can be filled with suitably symbols and/or combinations of symbols and/or temporal sequences of symbols implementing models of different types, hence adapted and/or personalized during the setup phase in order to include specific characteristics, habits, customs and practices of the assisted person (activities schedule, gestures, ranges of measured quantities and so on, as described in the following).

Furthermore, the system itself, during monitoring, can update symbols and/or combinations of symbols and/or temporal sequences of symbols in the assertional part of the taxonomic data structure, on the base of observations, under supervision of responsible persons or trained personnel. The symbols and/or combinations of symbols and/or temporal sequences of symbols and in particular their truth vales in this way updated referred to actions and their modifications in time can also be made available to healthcare personnel to control the evolution of diseases and/or impairments and/or of the simple aging of the assisted person.

With respect to the communication among devices, this takes place preferably using the original protocols, such as those based on IEEE 802, Bluetooth, UWB 868 MHz, Radio-Frequency IDentification (RFID, ISO/IEC 18000), and further modifications and evolutions, which interface all, or partially, the devices and, given their feature of being open to any user, are able to guarantee security, expandability, and connection to external systems, such as for example, a smartphone or other digital devices.

BRIEF DESCRIPTION OF THE DRAWINGS

These and other features and advantages of this invention result more clearly from the following description of a few examples illustrated in the attached figures, where.

DETAILED DESCRIPTION OF EMBODIMENTS OF THE INVENTION

Figure 1:
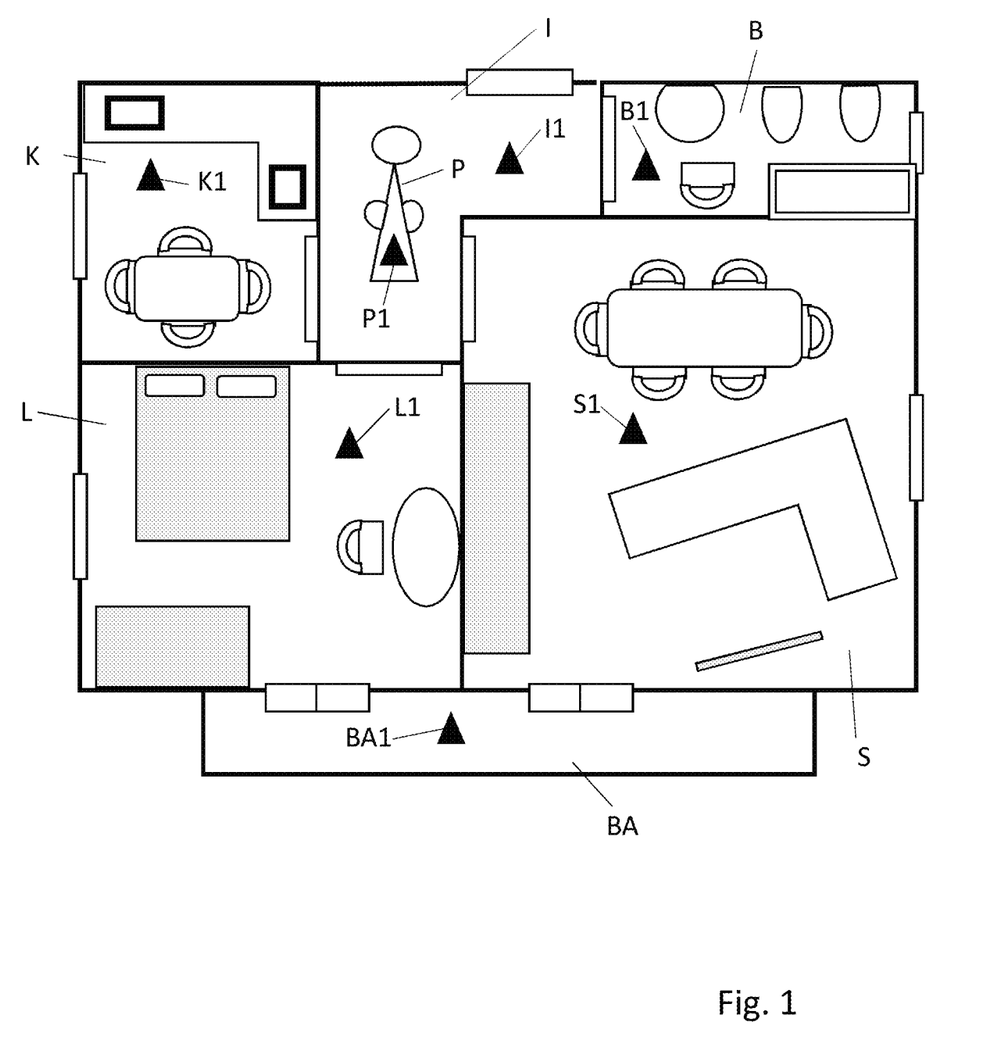
FIG. 1 schematically illustrates an example of the system according to the present invention in which the aforementioned system is applied to a delimited domestic environment.

The environment illustrated in FIG. 1 is related to a domestic environment that is obviously delimited. However, as it will be made clear from the description that follows, such example shall not be considered to be limiting, since the environment can also be a non delimited outdoor environment, being in the latter case the environmental sensors constituted by sensors already available also for other reasons, such as, for example but not only, cameras, light sensors, temperature sensors, etc. Furthermore, the monitored person's position can be tracked using such localization systems as the GPS or RFID or also using the cellular network and/or also using security cameras and/or cameras for traffic control. In this case the communication between the wearable devices to determine the posture and/or the physiological parameters and other system devices can take place using a portable device such as a mobile phone, a smartphone or similar digital devices.

Therefore, features described with respect to a domestic environment, but which can be foreseen also in the conditions of the aforementioned outdoor environment, are intended to be described by analogy also in outdoor, not limited and/or not delimited environments.

With respect to FIG. 1, the domestic environment is represented by the map of an apartment comprising different rooms, referred to as entrance hall I, kitchen K, bathroom B, bedroom L, living room S and balcony BA. Each of these rooms is furnished using furniture reflecting the room's function and comprises at least an entrance door, typically a window and/or at least one French window, for example to access the balcony BA.

Furthermore, typically a domestic environment includes a water supply system, a power supply system, possibly also a methane supply system, a heating system and/or a system to generate and distribute hot water, as well as the related measurement and control units.

A person living in the domestic environment is referred to as P.

The system according to the present invention foresees that the domestic environment be provided with different sensors able to acquire data related to one or more environmental parameters, which are indicated respectively with the "triangle" graphic sign and identified with the symbol that denotes the room where the sensors are located, and a number. In particular, the sensors to be located in the kitchen are indicated as a whole as K1, those in the bathroom as B1, those in the entrance hall as I1, those in the bedroom as L1, those in the living room as S1 and those in the balcony as BA1.

An essential type of sensors and/or combination of sensors is constituted by sensors to detect the presence of the monitored person, of their position and the variation of their position over time, for what concerns both position itself, but also the speed of variation and/or accelerations and/or decelerations.

These measurements can be combined with a digital model or virtual topological map of the domestic environment, possibly comprising also the position of several doors, windows and/or similar and/or at least several furniture elements, as well as the bathroom and/or the kitchen, and represented in the data structure of taxonomic type by means of symbols and/or combinations of symbols.

Figure 2:
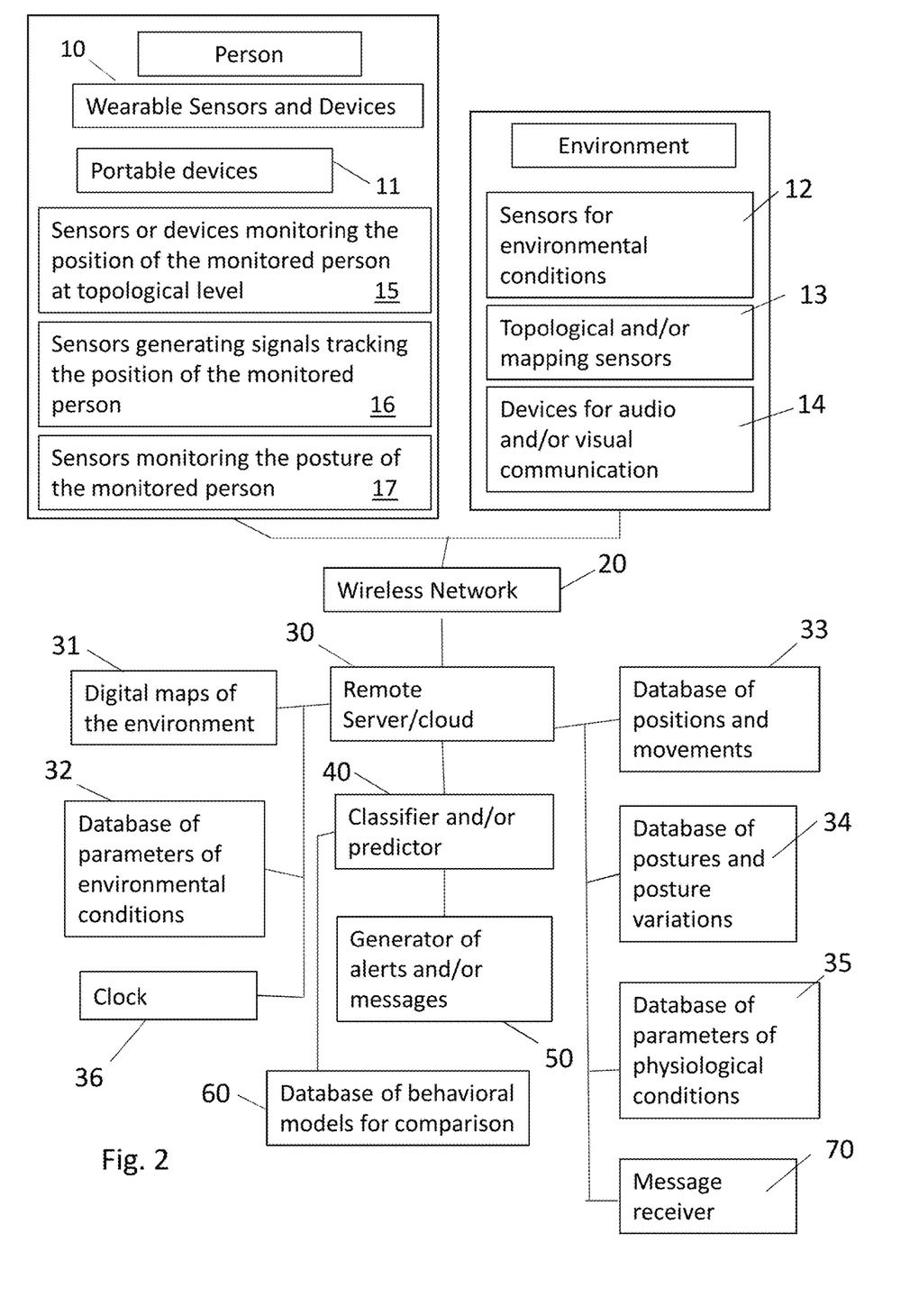
FIG. 2 illustrates a block-diagram of an example of the system according to the present invention.

With respect to FIG. 2, this map can be pre-constituted and stored in a data structure that is loaded in a server's memory and/or in a remote server and/or in a cloud server and/or in an assisted person's portable system, such as a mobile phone, a smartphone or similar digital device.

Thanks to this time-based position information and with reference to the virtual map of the environment, it is possible to localize, even precisely, the monitored person as well as to track his/her motion.

The indications of the sensors separated for each room do not have to be intended as limiting with respect to the fact that at least a number of sensor types could be physically located only in one or a few rooms and could extend their sensing range also to rooms where they are not physically present.

Environmental sensors can be of any given type and, as an example, they can include one or more sensors of the following typologies: temperature sensors, acoustic sensors, light sensors, smoke or gas sensors, sensors to detect the presence of liquids on the floor, water flow sensors, power consumption sensors, sensors to detect opening and/or closing of doors and/or windows and/or French windows or similar.

According to an additional refinement of the system according to the present invention, it is possible to foresee environmental sensors able to determine the environment's topological conditions or at least part of them, and which allow for the automated generation of a digital map of the environment where the assisted person is present.

This is particularly important when operating in outdoor, non-delimited environments. In this case, it is possible, in order to achieve the automated generation of a digital map of the environment, to use also sensors already available in the area to map the environment, such as, for example, cameras for traffic monitoring, security cameras and/or other sensors. Just in case, this information can be combined with other information related to street maps and/or topographic or similar, which can downloaded to navigation systems such as those available in mobile phones or in smartphones.

The monitored person denoted as P wears one or more wearable and/or portable sensors symbolically represented by triangle P1 in FIG. 1.

These sensors can be of any types and can include sensors of one or more physiological parameters, and also sensors to detect posture and/or its variations and/or sensors to detect motions executed by the monitored person. Also for such posture and/or movement variations, data are collected as a functions of time to determine the possible speed of execution related to posture variations and/or motions and possibly also to measure accelerations and/or decelerations.

In addition to wearable sensors, the monitored persons can stably carry with them a communication and/or computation device, i.e., able to execute programs and applications, such as smartphones, PDAs or similar digital devices.

As an additional improvement of the system according to the present invention, the communication device can be a Google Watch or an Apple Watch or a similar digital device, which acts as a kind of satellite device of a portable communication device such as, for example, a smartphone or a similar digital device.

For the sensors and the additional detection and personal communication devices described above, it is advantageous to use at the best of their characteristics already existing and largely commercially available devices.

In the case of these devices, it is important that they are provided with communication interfaces according to one or more existing communication protocols (or compatible with new standards not yet existing at the moment the present invention is described), and that they are suitable to be part of device networks, all of them communicating with each other.

The use of standard network protocols allows the system according to the present invention to be very easily scalable and modular and relatively low-cost, therefore allowing for progressively expanding the system itself as long as the assisted person's needs expand in their turn.

When monitoring an outdoor environment, the system according to the present invention foresees that a portable communication device, for instance a mobile phone and/or a smartphone and/or similar digital devices, play the role of access point for the assisted person's wearable devices towards the system's network.

In case of outdoor or non-delimited environments, this communication device keeps the link between the person and the system according to the present invention.

In case the system according to the present invention is implemented as an algorithm coded into a software under the form of instructions for a processor and memorized in a server and/or a remote server and/or distributed in a cloud server, and/or in a portable device of the monitored person, like a mobile phone, a smartphone or similar digital devices, being in this last case an application, for instance constituted by a software application executed on a smartphone or other portable communication device, then it is possible to distribute the functions of the system itself partially in the server and/or the remote server and/or the cloud server and partially in the portable device of the assisted person, such that to guarantee in any conditions a minimum level of connection and functionalities of the aforementioned system.

As indicated in FIG. 2, in a schematic way the wearable devices and the portable systems denoted 11 are connected in a network with environmental sensors denoted 12, 13 or 14, also using a wireless communication unit denoted 20 and using standard or even personalized protocols, with a processing unit denoted 30 that can be a server and/or a remote server and/or a cloud server and/or the monitored person's portable device denoted 11. Wearable sensors and devices include sensors or devices 15 monitoring the position of the monitored person at the topological level, sensors 16 generating signals that track the position of the monitored person, and sensors 17 monitoring the posture of the monitored person.

Data collected by sensors such as the digital maps denoted 31, the environmental parameters denoted 32, data about positions and movements denoted 33, data about posture and its variations denoted 34, data about physiological conditions denoted 35 are stored in corresponding data structures of taxonomic type, as described in the previous. A clock denoted 36 associates data with time stamps and duration measurements, therefore adding information able to associate to symbols and/or to combinations of symbols and/or to temporal sequences of symbols in the assertional part of the taxonomic data structure also information that allows interpreting data associating symbols with a certain type of voluntary or accidental behavior.

By synchronizing the timing of detection of the various data from the various sensors it is possible to correlate at least part of the symbols and/or to combinations of symbols and/or to temporal sequences of symbols in the assertional part of the taxonomic data structure in order to define more precisely the behavior of the person being monitored.

Considering an example referring to the figures, the system according to the present invention correlates the location of the assisted person located in a particular room, such as the kitchen for example, and/or with a place inside that room, such as "near the stove". At the same time, a given posture is detected as well as the execution of certain movements of the body of the said person. Moreover it is possible to detect measures of gas or electricity use (depending on the stove type).

The duration and the execution speed of some movements can be also monitored.

It is also possible to correlate the measurements with the data related to the monitored person's physiological parameters.

If the data are compatible with each other it can be considered at a first instance that the behavior is appropriate and not unusual.

Furthermore, having access to models that encode behaviour patterns known as standard and healthy for the assisted person in terms of symbols and/or combinations of symbols and/or temporal sequences of symbols, which can be used to understand whether symbols and/or combinations of symbols and/or temporal sequences of symbols representing data coming from sensors in the assertional part of the data structure do correspond to dangerous situations and/or bad habits of the person, it is possible to put into relation the measured data with parameters of the standard models to classify what type of activity is carried out by the said person and if the same activity is carried out in the normal way.

A further example is the detection of the assisted person in the bedroom, possibly in a position corresponding to the bed and, at the same time, an absence of movement and/or a reduced number of movements and/or the physiological parameters compatible with a condition of rest. An ambient light sensor can also complete the picture by detecting low light intensity, or its absence, compatible with a condition of rest.

Advantageously, in addition to generating a set of models encoding standard behavioral models related to the healthy characteristics, habits, customs and practices of the assisted person by means of symbols and/or combinations of symbols and/or temporal sequences of symbols, common for the most part of people, or referring to standard behavioral models related to every day custom actions specific to the assisted person, the system, according to the present invention, can provide a classifier of symbols and/or combinations of symbols and/or temporal sequences of symbols corresponding to the data detected by the sensors, denoted 40 in the figure, being such models suitably coded, or the result of a learning process or personalization; this process can be carried out at in the installation and/or setup phase of the said system, and can take into account all feedbacks that operators of the said system give about performed activities of the assisted person.

The system according to the present invention can also provide for a unit generating alerts and/or messages and/or alarms, denoted 50; such messages can be generated according to the type of behavior or detected situation, and sent as requests for help to the outside, also operated by personnel not specialized, such as relatives, medical or paramedical personnel, personnel trained to deal with emergencies, firefighters, neighbors, etc. The messages to the monitored person, as to say, the aforementioned dialogue, can be either a message without no feedback expected from the recipient, or, preferably, with a feedback expected from her/him. The system according to the present invention dialogues with the assisted person using a limited form of natural language, using speech synthesis, to decide, using the aforementioned dialogue, whether the monitored person is in a dangerous situation, the danger gravity, or simply to remind the assisted person about some important information, for example suggesting or pushing the person to carry out some suitable activity, recreational activities or typical of everyday life.

The dialogue method is such that questions (by the system) and relative answers (by the monitored person), encoded by the system according to the present invention as symbols and/or combinations of symbols and/or temporal sequences of symbols, and classified by inferential algorithms typical of logical formalisms like Description Logic, can be put into relation with the behavioral models stored in the terminological components of the data structure, in order to understand the person's state and the possible danger situations, or simply any attention needed.

In particular, when it is necessary to communicate with the assisted person it is possible to foresee using adequate passive communication devices, possibly commercially available, for diffusing such messages e.g., through the home TV, or suitable fixed devices in the home, or ad hoc portable devices, or by means of the portable device for monitoring, or devices to which the same monitored person can respond and communicate or send also requests; those devices can be ad hoc communication equipment, even industry standard and interfaced to the system, or the portable monitoring device itself worn by the assisted person.

Dialogues with the assisted person can be either predefined and formally defined as symbols and/or combinations of symbols and/or temporal sequences of symbols, as well as rule-based models and/or models based on formal grammars, as well as designed in the set up or installation phase by a suitably expert supervising person.

With regard to the part of the taxonomic data structure representing behavioral models, in particular those models representing habits specific to the assisted person, this can be done by providing the system with a learning phase performed on a limited number of experimental users and for a limited period of time.

The data structure of taxonomic type, which comprises the normative models for the actions of the assisted person, the model of the environment in which the assisted person is monitored, normative models for the typical habits of the person, the models possibly based on formalism rules for the generation of messages and/or announcements and/or alarms, possibly models based on rule-based formalisms and/or possibly related to formal grammars, together with the components of the data acquisition system, translation of data originating from sensors in appropriate symbols and/or combinations of symbols and/or temporal sequences of symbols, the classification methods typical of the Description Logics formalisms, the components of the dialogue management system with the assisted person or of the alarm communication, are the minimal constituents of the algorithm which implements the system according to the present invention.

The system according to the present invention is able to understand the level of welfare of the assisted person according to his/her habits and even customized parameters, to predict critical situations, to intervene promptly in case of danger, to dialogue with the person to increase the understanding of what is happening, to accumulate significant data to support further follow-up assistance, to understand gestures, movement, position of the person, to learn calibrated changes to his/her habits, to handle the requests for help outside of the home (relatives, trained personnel, public and/or private care institutions, police etc.), to support a personalized adaptation, even by non specialized people, such as relatives of the person being monitored, always complying with the aforementioned principle of intrinsic safety.

The taxonomic data structure can be tailored with respect to the assisted person in the set up phase, by a properly expert supervisor, or in a successive phase; this adaptation can be made easy with a suitably usable software interface, textual and/or graphical. The interface, suitably designed, can allow even non trained persons to carry out tailoring the system according to the present invention.

In its basic form the system according to the present invention includes the following functional characteristics:

Monitoring the position of the assisted person at topological level (e.g., "in the kitchen", "near the bed", or "close to the door").

This implies the presence of devices to be placed in the monitored environment and a topological model of the environment in which the assisted person acts.

As mentioned previously, the system according to the present invention can use sensors and/or transponders and/or similar digital devices to detect the presence of the person in certain areas and can also include an automatic mapping system able to deduce the topology of the environment. This can be achieved also through the use of sensor networks and the development of techniques to generate the map of an unknown environment.

Monitoring posture of the assisted person at discrete level (e.g., "standing", or "sitting").

To recognize the posture and/or the transition between postures (including a fall) it is possible to use wearable sensors incorporated in accessories (for example, but not limited to, watches and/or tags and/or eyeglasses and/or belts) and/or clothes.

Such wearable sensors require using algorithms for the detection and classification of postures, adaptable to the monitored person.

Interaction between the monitoring system and the person (assisted also by means of systems based on vocal dialogue).

This case requires the presence of microphones and speakers in the devices, distributed and/or wearable.

The system according to the present invention can use, or interface, technologies for voice interaction, even commercially available, in particular to activate communication in response to specific events and/or emergency situations.

The voice interaction can be further integrated with the proactive analysis of situations, and techniques of the so-called "speech recognition" and "speech production".

To these basic features some advanced features and options can be added such as, for example, the following one:

Motion analysis to detect particular activities (e.g., "drink", or "seated for a long time" or "staying in bed for a long time"). These activities include:

the monitoring of the posture of the assisted person and of other unusual movement patterns;

the classification of temporal series of data related to the above mentioned movements compared to templates predefined or adapted to the person by using algorithms based on logic formalisms and/or able to learn from data.

Thanks to this feature it is possible to integrate the functionalities described above with an analysis of the activity compared with models of cognitive impairments or other disabilities, based on the monitoring data of the daily activities of the person and on comparison with behavioral models adapted to the person, in order to identify deviations from the normative behavior models.

In this case it is also possible to perform an adaptation in time of the monitoring schemes (e.g., to evaluate the degradation over time of the person's physical, neurological and cognitive functions).

This additional functionality includes the steps of adaptation of customized standard models to the monitored person to new behavior patterns in carrying out usual activities, and/or of identifying new activities, which vary over time.

Thanks to possible learning mechanisms described in literature, such as for example classifiers and predictive algorithms, it is possible to obtain new and/or updated models from sensory data, and to adapt the monitoring system according to the present invention to the progressive degradation over time of the person's physical, neurological and cognitive functions.

Figure 3:
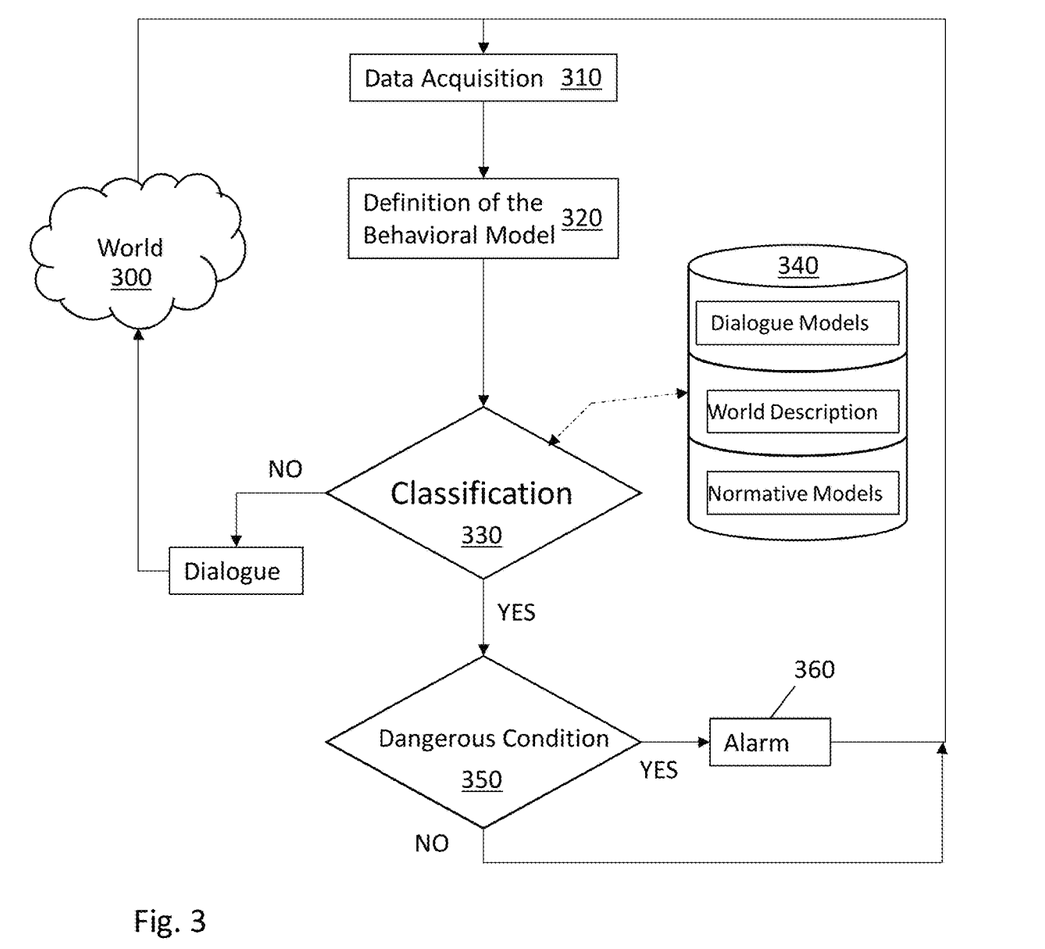
FIG. 3 illustrates a flow diagram of the algorithm which implements characteristics and functionalities of the system according to the present invention.

FIG. 3 illustrates a flow diagram of the algorithm that implements the features and functionality of the system according to the present invention.

Step 300 represents the environment in which the assisted or monitored user is active. In step 310 the data collected are acquired by one or more sensors. The step 320 provides for the interpretation of these data in accordance with a behavioral model.

The step 330 provides classification of the type and quality of data collected in relation to the behavioral model. In this case the database of normative data, the description of the environment and of dialogue models is marked with tag 340 and includes descriptions of the behavioral model. When the classification does not detect dangerous or abnormal behavior, the acquisition process continues. In case of abnormal behavior a dialogue is triggered with the assisted person, from which information is obtained by the dialog models based on the identification of the behavioral condition or of the specific behavioral tipology.

If the classification detects a condition of danger at the step 350, an alarm is generated (marked 360). Otherwise the classification continues with the data acquisition cycle.

The invention claimed is:

1. System for private monitoring and assistance of a monitored person, comprising:
   one or both of first sensors detecting parameters describing conditions of an environment where the monitored person is located, or second sensors detecting at least a position or a movement of the monitored person in the environment, and a posture of the monitored person and his/her physiological parameters, wherein the first and the second sensors comprise:
   third sensors or devices monitoring the position of the monitored person at a topological level, the third sensors generating signals tracking the position of the monitored person in time and within a digital topological model of the environment in which the monitored person is located;
   fourth sensors heterogeneous from the third sensors and monitoring the posture of the monitored person and variations thereof in time, the fourth sensors providing status signals corresponding to predetermined postures or signals of the time variation of the posture of the monitored person;
   and
   a processing unit configured to perform processing steps according to a classification algorithm which is coded in instructions executable by said processing unit, to classify one or more of different symbols, combinations of the symbols, or temporal sequences of the symbols, the symbol being logical symbols, and which provides the following operational steps:
   representing, with the symbols, combinations of the symbols, or temporal sequences of the symbols, data from said third and fourth sensors;
   determining whether the symbols, combinations of symbols, or temporal sequences of the symbols correspond to normative behavior patterns described in a data structure represented by a classification formalism or an equivalent formalism from an expressive and computational point of view;
   classifying the symbols, combinations of symbols, or temporal sequences of the symbols as compatible or not compatible with respect to the normative behavior patterns describing typical everyday situations or even at a level of specific customs and habits of the monitored person;
   deciding whether to activate a procedure for dialogue with the monitored person in order to acquire additional data from the third and fourth sensors to be associated with appropriate logical symbols, combinations of logical symbols, or temporal sequences of the logical symbols; and deciding whether to activate alarm procedures depending on type and severity of the alarm.

2. The system according to claim 1, wherein the normative behavior patterns are achieved by providing in the system a learning phase performed on a limited number of experimental users and for a limited period of time, the learning phase collecting information on behavioral characteristics of the monitored person in relation to usual conditions of behavior, habit, or a synthesis of a suitable number of said normative behavioral patterns.

3. The system according to claim 1, wherein the data relating to one or more of the parameters of position of the monitored person, the monitored person's movement in the environment, or the monitored person's posture and variation thereof are combined with the data related to physiological parameters of the monitored person detected by the fourth sensors or a variation of the physiological parameters over time.

4. The system according to claim 1, wherein environmental condition sensors are also used, the environmental sensors being selected from the group consisting of temperature sensors, acoustic sensors, light sensors, smoke or gas sensors, sensors detecting a presence of a liquid on a floor, water flow sensors, power consumption sensors, sensors detecting opening and/or closing of a doors or a window.

5. The system according to claim 1, wherein the classification algorithm is encoded as instructions in a memorized program in a memory and is callable from the memory and executable by the processing unit, whereby the classification algorithm configures the processing unit as a control unit that carries out a control procedure which integrates a classification of activities recorded from the data of the position of the monitored person in the environment, the variation of the position or posture, or a variation of the same with the data of the physiological parameters or of the or the data of environmental conditions, thus increasing precision of the classification and the conditions of said monitored person.

6. The system according claim 1, wherein, when the classification of the symbols, the combinations of said symbols, or temporal sequences of said symbols indicates a condition of abnormal behavior of the monitored person or outside behavior of an usual behavioral patterns or an otherwise dangerous situation, making it possible to automatically generate alarms to be sent to a number of people and organizations decided during installation or setup phases said people having competence to intervene addressing situations recognized by the classification procedure.

7. The system according to claim 1, further comprising means for direct passive communication with the monitored person.

8. The system according to claim 1, wherein symbols, combinations of symbols, or temporal sequences of the symbols corresponding to activities of the monitored person are classified periodically, being measured evolutions of cognitive ability or the physiological conditions of said monitored person, thus enabling a prompt intervention not only to protect the monitored person from a condition of immediate danger, but also to put therapeutic foundations necessary to cope with a worsening of her the monitored person's conditions, in a still relatively initial moment of a possible pathology.

9. The system according to claim 1, wherein the system comprises a modular and scalable architecture with four levels, which comprise:
  i. a layer consists of a hardware infrastructure;
  ii. a layer consists of the classification algorithm, executed on the hardware infrastructure, which implements both a classification procedure based on a taxonomic data structure and a dialogue with the monitored person; and
  iii. a layer constituted by a data structure containing symbols representing models, normative behavioral patterns, symbols which describe some characteristics of an environment, or symbols which refer to possible dialogues described in a logical formalism based on description logics;
  wherein a data structure includes:
    a. models that connect sensory data to the symbols, combinations of the symbols, or temporal sequences of the symbols that refer to actions executed by the monitored person and the postures of the monitored person;
    b. models that connect the sensory data to the symbols, the combinations of the symbols, or the temporal sequences of the symbols that refer to typical habits of the monitored person;
    c. a model that represents the environment in which the monitored person lives and acts, based on characteristics thereof using the symbols, the combinations of the symbols, or the temporal sequences of the symbols, for localization of the monitored person at topological level;
    d. models that encode normative aspects related to healthy habits for the monitored person by the symbols, the combinations of the symbols, or the temporal sequences of the symbols, to define whether the symbols, the combinations of the symbols, or the temporal sequences of the symbols representing the data from the first and the second sensors correspond to potentially dangerous situations or to bad habits of the monitored person;
    e. rule-based models that based on a classification of the symbols, the combinations of the symbols, or the temporal sequences of the symbols generate alarms or messages, or receive feedback for dialogues with the monitored person; and
    f. models related to rules or based on structures related to formal grammars for encoding dialogues with the monitored person using the symbols, the combinations of the symbols, or the temporal sequences of the symbols; and
  iv. a layer of communication and sharing of the data among system hardware devices and with external communication systems;
  further comprising a communication network that uses standard open protocols for interfacing with all the hardware components of the system.

10. A method for monitoring and carrying out private assistance of people of all ages, in situations where the people cannot be considered as independent, the method comprising:
  a. generating a taxonomic data structure populated with symbols, combinations of symbols, or temporal sequences of the symbols which refer to various types of models, the symbols being logical symbols, and which require data on a position of an assisted person related to behaviors in a predetermined environment, movements, or displacements of the assisted person in the predetermined environment, posture of the assisted person, or the changes in the posture in carrying out activities;
b. representing and managing the symbols, the combinations of the symbols, or temporal sequences of the symbols related to the activities of daily life, both simple and composed by different actions or postures, together the time information and information about all relevant locations;
c. generating a virtual map of an environment in which the assisted person is present and a representation of the environment in the taxonomic data structure using the symbols or combinations of the symbols;
d. determining position or tracking movements of the assisted person with reference to time, and determining the posture the changes of the posture of the assisted person in time;
e. generating a behavioral model of the assisted person from data provided by sensors and represented by the symbols, the combinations of the symbols, or the temporal sequences of the symbols in the taxonomic data structure;
f. classifying typology of behavior and adequacy of the behavior of the assisted person compared to normative patterns of the behavior represented in the taxonomic data structure;
g. performing step f, but in relation to sequences or compositions of the actions as defined in point b;
h. generating and issuing audio or visual communications to assistance personnel or to the assisted person according to a type of the behavior detected during classification and to appropriateness of the behavior with normative behavior patterns represented in the taxonomic data structure; and
i. generating, issuing, and managing, by a classification algorithm, suitable vocal dialogues such that that the classification algorithm enables, by analyzing feedback, an improvement in a monitoring of the assisted person, inferring the assisted person's state of health, recognizing an existence of dangerous situations, or identifying most important needs in case of a rescue operation.

11. The method according to claim 10, further comprising detecting physiological parameters of the assisted person and environmental parameters, and integrating the physiological and environmental parameters in the behavioral model, being the physiological and environmental parameters synchronized with reference to an instant of detection or a duration in time.

* * * * *